(12) United States Patent
Zhang et al.

(10) Patent No.: US 9,816,882 B2
(45) Date of Patent: Nov. 14, 2017

(54) ELECTRONIC SKIN, PREPARATION METHOD AND USE THEREOF

(71) Applicant: SUZHOU INSTITUTE OF NANO-TECH AND NANO-BIONICS (SINANO), CHINESE ACADEMY OF SCIENCES, Suzhou, Jiangsu (CN)

(72) Inventors: Ting Zhang, Jiangsu (CN); Xuewen Wang, Jiangsu (CN); Zuoping Xiong, Jiangsu (CN); Yang Gu, Jiangsu (CN); Wen Gu, Jiangsu (CN)

(73) Assignee: SUZHOU INSTITUTE OF NANO-TECH AND NANO-BIONICS (SINANO), CHINESE ACADEMY OF SCIENCES, Suzhou (CN)

( * ) Notice: Subject to any disclaimer, the term of this patent is extended or adjusted under 35 U.S.C. 154(b) by 83 days.

(21) Appl. No.: 14/764,165

(22) PCT Filed: Jan. 28, 2014

(86) PCT No.: PCT/CN2014/071631
§ 371 (c)(1),
(2) Date: Jul. 28, 2015

(87) PCT Pub. No.: WO2014/117724
PCT Pub. Date: Aug. 7, 2014

(65) Prior Publication Data
US 2016/0011063 A1  Jan. 14, 2016

(30) Foreign Application Priority Data

Jan. 29, 2013 (CN) .......................... 2013 1 0034478
Oct. 24, 2013 (CN) .......................... 2013 1 0507497
(Continued)

(51) Int. Cl.
*G01L 1/18* (2006.01)
*G06F 3/041* (2006.01)
(Continued)

(52) U.S. Cl.
CPC ............ *G01L 1/18* (2013.01); *A61B 1/00149* (2013.01); *A61B 3/16* (2013.01); *A61B 5/021* (2013.01);
(Continued)

(58) Field of Classification Search
CPC ........ A61B 1/00149; A61B 2562/0204; A61B 2562/0285; A61B 34/30; A61B 3/16;
(Continued)

(56) References Cited

U.S. PATENT DOCUMENTS 3,565,195 A * 2/1971 Miller ...................... G01G 7/06
177/210 C
3,875,481 A * 4/1975 Miller ...................... G01G 7/06
177/210 C
(Continued)

FOREIGN PATENT DOCUMENTS

DE  19533756 A1  3/1997

OTHER PUBLICATIONS

Yamada, Takeo, et al. "Hierarchical three-dimensional layer-by-layer assembly of carbon nanotube wafers for integrated nanoelectronic devices." Nano letters 12.9 (2012): 4540-4545.*
(Continued)

*Primary Examiner* — Lisa Caputo
*Assistant Examiner* — Punam Roy

(57) ABSTRACT

The invention provides a piezoresistive electronic skin, a preparation method and a use thereof. The piezoresistive electronic skin uses carbon nanotube film as the conductive layer and uses materials provided with micro-nano patterns, such as polydimethylsiloxane, polyethylene terephthalate,
(Continued)

polyvinyl alcohol, polyvinyl formal, polyethylene, and so on, as the substrate, enabling the substrate has advantages of high flexibility and being pliable, and it needs low operating voltage and little power consumption, but has high sensitivity and short response time. More importantly, the invention uses the patterned flexible substrate as the basis, greatly improving the sensitivity of electronic skin reacting to tiny applied force from outside. The invention also provides a capacitive electronic skin and a preparation method thereof. Further, the invention also provides a use of the piezoresistive electronic skin or the capacitive electronic skin on speech recognition, pulse detection, medical robot, etc.

11 Claims, 9 Drawing Sheets

(30) Foreign Application Priority Data

Oct. 24, 2013 (CN) .......................... 2013 1 0508179
Dec. 17, 2013 (CN) .......................... 2013 1 0693411

(51) Int. Cl.
| | | |
|---|---|---|
| G01L 1/14 | (2006.01) | |
| A61B 5/11 | (2006.01) | |
| A61B 5/024 | (2006.01) | |
| A61B 5/00 | (2006.01) | |
| A61B 34/30 | (2016.01) | |
| A61B 1/00 | (2006.01) | |
| A61B 3/16 | (2006.01) | |
| A61B 5/0205 | (2006.01) | |
| A61B 5/021 | (2006.01) | |
| B29C 41/02 | (2006.01) | |
| B29C 41/42 | (2006.01) | |
| B29C 65/00 | (2006.01) | |
| B29K 83/00 | (2006.01) | |
| B29L 9/00 | (2006.01) | |
| B29L 31/34 | (2006.01) | |
| B29L 31/00 | (2006.01) | |

(52) U.S. Cl.
CPC ............ *A61B 5/024* (2013.01); *A61B 5/0205* (2013.01); *A61B 5/11* (2013.01); *A61B 5/4803* (2013.01); *A61B 34/30* (2016.02); *B29C 41/02* (2013.01); *B29C 41/42* (2013.01); *B29C 65/00* (2013.01); *G01L 1/14* (2013.01); *G06F 3/041* (2013.01); *A61B 2562/0204* (2013.01); *A61B 2562/0285* (2013.01); *B29K 2083/00* (2013.01); *B29K 2995/0003* (2013.01); *B29K 2995/0005* (2013.01); *B29L 2009/005* (2013.01); *B29L 2031/34* (2013.01); *B29L 2031/7546* (2013.01)

(58) Field of Classification Search
CPC ....... A61B 5/0205; A61B 5/021; A61B 5/024; A61B 5/11; A61B 5/4803; B29C 41/02; B29C 41/42; B29C 65/00; B29K 2083/00; B29K 2995/0003; B29K 2995/0005; B29L 2009/005; B29L 2031/34; B29L 2031/7546; G01L 1/14; G01L 1/18; G06F 3/041
See application file for complete search history.

(56) References Cited

U.S. PATENT DOCUMENTS

| | | | | |
|---|---|---|---|---|
| 4,509,527 A * | 4/1985 | Fraden | .................. | A61B 5/113 600/484 |
| 4,654,546 A * | 3/1987 | Kirjavainen | ........... | H04R 23/00 29/594 |
| 4,852,443 A * | 8/1989 | Duncan | ................ | G10H 1/0551 200/600 |
| 4,986,136 A * | 1/1991 | Brunner | .................. | G01L 1/146 361/278 |
| 5,642,015 A * | 6/1997 | Whitehead | ............ | B06B 1/0292 310/309 |
| 5,977,685 A * | 11/1999 | Kurita | .................... | C08G 18/10 310/311 |
| 6,047,203 A * | 4/2000 | Sackner | ............. | A41D 13/1281 600/301 |
| 6,216,545 B1 * | 4/2001 | Taylor | .................. | A61B 5/1036 73/862.046 |
| 6,341,504 B1 * | 1/2002 | Istook | .................. | A61B 5/0002 2/69 |
| 6,543,110 B1 * | 4/2003 | Pelrine | .................. | F04B 35/045 29/25.35 |
| 6,555,945 B1 * | 4/2003 | Baughman | .............. | F03G 7/005 136/291 |
| 6,809,462 B2 * | 10/2004 | Pelrine | .................... | A63H 3/365 310/319 |
| 7,573,064 B2 * | 8/2009 | Benslimane | ............ | G01L 1/142 257/306 |
| 7,808,163 B2 * | 10/2010 | Benslimane | ............ | B81B 3/007 310/365 |
| 7,814,801 B2 * | 10/2010 | Inamori | .................... | G01B 7/18 73/849 |
| 7,843,111 B2 * | 11/2010 | Benslimane | ............ | B81B 3/007 310/311 |
| 7,880,371 B2 * | 2/2011 | Benslimane | .......... | H01L 41/083 310/367 |
| 7,935,414 B2 * | 5/2011 | Ounaies | .................. | B32B 27/20 428/141 |
| 7,954,385 B2 * | 6/2011 | Raisanen | .................. | G01L 1/14 73/780 |
| 7,984,544 B2 * | 7/2011 | Rosenberg | ......... | A63B 71/0605 29/595 |
| 8,181,338 B2 * | 5/2012 | Benslimane | .......... | B81B 3/0021 29/825 |
| 8,322,224 B2 * | 12/2012 | Hou | .......................... | G01L 1/18 73/727 |
| 8,390,589 B2 * | 3/2013 | Hu | .......................... | G06F 3/044 178/18.01 |
| 8,431,080 B2 * | 4/2013 | Liu | .................... | B01L 3/502707 257/417 |
| 8,692,442 B2 * | 4/2014 | Poole | .................. | H01L 41/0472 310/328 |
| 8,943,908 B2 * | 2/2015 | Liu | .......................... | G01L 1/06 73/172 |
| 9,231,186 B2 * | 1/2016 | Busgen | ..................... | F15D 1/12 |
| 9,454,255 B2 * | 9/2016 | El Kallassi | ......... | G01R 27/2605 |
| 2002/0175594 A1 * | 11/2002 | Kornbluh | ......... | B60G 17/01941 310/317 |
| 2003/0006669 A1 * | 1/2003 | Pei | ........................ | A61M 5/142 310/309 |
| 2003/0066741 A1 * | 4/2003 | Burgess | .................. | H01H 3/142 200/61.43 |
| 2004/0012301 A1 * | 1/2004 | Benslimane | ............ | B81B 3/007 310/311 |
| 2004/0012913 A1 * | 1/2004 | Andelman | ............ | C02F 1/4691 361/503 |
| 2004/0124738 A1 * | 7/2004 | Pelrine | .................... | F02G 1/043 310/307 |
| 2005/0040736 A1 * | 2/2005 | Topliss | .................. | H01L 41/098 310/367 |
| 2005/0104145 A1 * | 5/2005 | Benslimane | ............ | G01L 1/142 257/415 |
| 2006/0016275 A1 * | 1/2006 | Gravesen | ................. | G06F 3/044 73/862.042 |

(56) References Cited

U.S. PATENT DOCUMENTS

| | | | | |
|---|---|---|---|---|
| 2006/0258914 | A1* | 11/2006 | Derchak | A61B 5/04325<br>600/300 |
| 2006/0275907 | A1* | 12/2006 | Glocker | A61B 5/021<br>436/70 |
| 2007/0277356 | A1* | 12/2007 | Benslimand | H01L 41/0836<br>29/25.35 |
| 2008/0265709 | A1* | 10/2008 | Clausen | H01L 41/083<br>310/300 |
| 2009/0064476 | A1* | 3/2009 | Cross | H01L 41/083<br>29/25.35 |
| 2010/0072565 | A1* | 3/2010 | Liu | B01L 3/502707<br>257/417 |
| 2011/0240621 | A1* | 10/2011 | Kessler | G01N 25/72<br>219/200 |
| 2012/0062245 | A1* | 3/2012 | Bao | H01L 29/84<br>324/661 |
| 2012/0234105 | A1* | 9/2012 | Taylor | G01L 1/18<br>73/862.046 |
| 2013/0041235 | A1* | 2/2013 | Rogers | A61B 5/6867<br>600/306 |
| 2013/0091961 | A1* | 4/2013 | Taylor | B32B 5/26<br>73/862.541 |
| 2013/0113057 | A1* | 5/2013 | Taylor | G01L 1/18<br>257/417 |
| 2013/0228370 | A1* | 9/2013 | Seike | H01B 1/22<br>174/9 F |
| 2013/0285970 | A1* | 10/2013 | Ahn | G06F 3/044<br>345/173 |
| 2014/0090488 | A1* | 4/2014 | Taylor | G01L 1/18<br>73/862.625 |
| 2014/0376158 | A1* | 12/2014 | Kim | H01G 11/24<br>361/502 |
| 2015/0059486 | A1* | 3/2015 | Choong | G01L 1/2206<br>73/727 |
| 2015/0248159 | A1* | 9/2015 | Luo | G06F 3/014<br>345/156 |
| 2016/0349134 | A1* | 12/2016 | Jeon | G01L 19/0092 |

OTHER PUBLICATIONS

Robert, Colin, Jean Francois Feller, and Mickael Castro. "Sensing skin for strain monitoring made of PC-CNT conductive polymer nanocomposite sprayed layer by layer." ACS applied materials & interfaces 4.7 (2012): 3508-3516.*

Pang, Changhyun, et al. "A flexible and highly sensitive strain-gauge sensor using reversible interlocking of nanofibres." Nature materials 11.9 (2012): 795-801.*

Zhang, Daihua, et al. "Transparent, conductive, and flexible carbon nanotube films and their application in organic light-emitting diodes." Nano letters 6.9 (2006): 1880-1886.*

Lee, Jung-Yong, et al. "Solution-processed metal nanowire mesh transparent electrodes." Nano letters 8.2 (2008): 689-692.*

Lipomi, Darren J., et al. "Skin-like pressure and strain sensors based on transparent elastic films of carbon nanotubes." Nature nanotechnology 6.12 (2011): 788-792.*

Mannsfeld, Stefan CB, et al. "Highly sensitive flexible pressure sensors with microstructured rubber dielectric layers." Nature materials 9.10 (2010): 859-864.*

Zaouk, Rabih, Benjamin Y. Park, and Marc J. Madou. "Fabrication of polydimethylsiloxane microfluidics using SU-8 molds." Microfluidic Techniques: Reviews and Protocols (2006): 17-21.*

International Search Report of PCT Patent Application No. PCT/CN2014/071631 dated May 12, 2014.

* cited by examiner

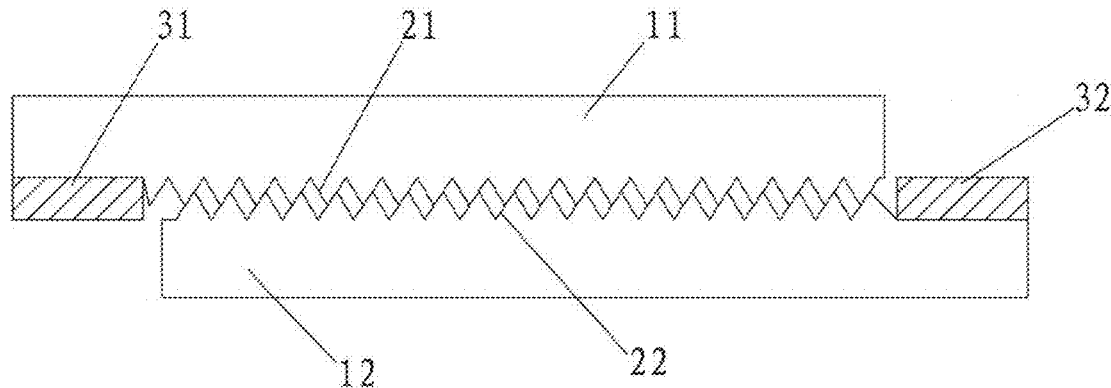

FIG. 1

```
Preparing two patterned flexible substrates, at least one
layer of which is polydimethylsiloxane film                          S1

Preparing a solution for the conductive layer, and coating
it to the patterned surfaces of the two flexible substrates
to form carbon nanotube films, respectively. Assembling
the conductive layers by making the patterned surfaces               S2
face to face to form a film device with conductive layers
being contacted with each other.

Forming upper, lower conductive electrodes respectively
on the two conductive layers by conductive material and
leading wires from the conductive electrodes, thereby
obtaining a piezoresistive electronic skin.                          S3
```

FIG. 2

ELECTRONIC SKIN, PREPARATION METHOD AND USE THEREOF

FIELD OF THE INVENTION

The present invention relates to the field of sensors, more particularly to an electronic skin, a preparation method and a use thereof.

BACKGROUND OF THE INVENTION

As automatic devices with artificial intelligence, robots have been more and more involved in people's daily lives and have replaced human to perform related work in hazardous industries such as high temperature, high pressure, explosive disposal, etc. By the integration of various sensors, the existing robot systems already have achieved a lot of human sensations, like vision, hearing and olfaction. However, the robot systems are faced with one of the most challenging problems all the time: how to get sensitive tactile sensation like human beings. The birth of electronic skin will bring the robot systems tremendous changes and will enable the robots to get more information from the external environment.

Since the University of Tokyo first suggested an electronic artificial skin using organic field-effect transistors (hereafter referred to as OFET electronic skin), some research groups in Japan and America have constructed the electronic skin based on organic field effect transistor, capacitive electronic skin as well as piezoresistive electronic skin successfully. However, the application ranges of these devices are limited due to complicated processing technic and device structures, bigger driving voltage, lower sensitivity or characteristics such as non-transparency and non-flexibility resulting from the use of rigid silicon-based materials. Therefore, it is necessary to provide an artificial electronic skin which has simple structure, high sensitivity, high accuracy and durability.

Along with the advent of conceptual products such as the GOOGLE GLASS (a trademark), the APPLE IWATCH (a trademark), and the like, wearable equipment comes to public attention with advantages such as high sensitivity, low cost, low power consumption, easy portability, more convenient user experience, and so on, extending functions that a personal computer (PC) and cell phone do not have. By the deep integration with software and hardware technology and by means of highly integrated intelligent terminal, wearable equipment not only creates smart personal life, but also builds smart city and even smart world, thereby bringing the life-style and consumption concept of human being revolutionary changes. There will be many varieties of wearable equipment in future, but all of which will be combined with sensor technology, taking the human body as a part of input or output process, then connecting the Internet by itself or by applications (APP) on the cell phone, and finally achieving intelligent human-machine interaction.

The electronic skin with nanostructure, ultrathin thickness, lighter weight, and flexibility similar to human skin is the most suitable material for constructing wearable equipment. Recently, the world-recognized top journal Nature has reported an ultrathin (2 μm) electronic skin with organic field-effect transistors (OFET) structure, which is lighter than feather and still works after being kneaded, stretched out, or drawn back. However, because of low carrier mobility of organic field-effect transistors (OFET) the electronic skin needs high working voltage and high power consumption, but has low sensitivity.

In addition, with the rapid development of communication technology and continuous progress of computer science and technology, speech recognition becomes a remarkable high-tech intelligent human-computer interaction technology, which involves multi-disciplines comprehensive technologies of phonetics, vocalism principle, microelectronic technology, computer information processing technology, speech processing technology, circuit and system, sense technology, and so on. The application thereof has become a competitive new high-technology industry.

The reported speech recognition technologies are usually based on methods of speech template, large vocabulary continuous speech recognition, acoustic model, etc. However, these traditional speech recognition technologies have lots of problems. For example, in circumstances of noisy environment, unclear pronunciation with accent or in dialect, or of a multitude of voices from multi-people at the same time, voice input will have a bad effect, low recognition rate and even will fail to be recognized. The main reason for these problems mentioned above is that traditional voice acquisition modules capture voices by collecting transmitted signals of voices in the air, while other acoustic sources around will interfere the collecting of voice data.

Moreover, in order to extract physiological and pathological information from the pulse waves of human body as the basis for clinical diagnose and treatment, a number of pulse monitors appear in recent years, such as portable electronic sphygmomanometer which can measure pulse. However, this kind of portable electronic sphygmomanometers use mini air pump to pressurize rubber pneumatic bag and need pressurizing process and depressurizing process in every single measurement, thereby having some problems, such as big size, uncomfortable user experience during pressurization and depressurization, low accuracy in the detection of pulse, disability of displaying a full waveform of pulse wave, etc. Some large sphygmographes, such as the COMPLIOR (a trademark) analyzer (France), have accurate measuring results and good repeatability, but are mainly used in specialist treatment and the study of epidemiology and are too expensive to use in household or popular portable medical services.

Furthermore, in order to meet the growing needs of people, it is very necessary to explore new applications in various fields for the electronic skin which is an electronic device with extremely high sensitivity.

SUMMARY OF THE INVENTION

One of the goals of the present invention is to provide a piezoresistive electronic skin with a completely new structure, which has advantages of low cost, low driving voltage, high sensitivity, short response time, high stability, etc.

In order to achieve the above goal, the present invention provides a piezoresistive electronic skin, comprising:

a plurality of overlapped flexible substrates;

a conductive layer arranged on contact surface of adjacent flexible substrates, at least one contact area of the conductive layer having non-planar structure; and conductive electrodes electrically connected with the conductive layer.

Preferably, at least one of the flexible substrates uses polydimethylsiloxane film, or, at least one of the flexible substrates is made of one or a combination of more of the follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), and high-polymer rubber materials.

Further, if the flexible substrate uses polydimethylsiloxane film, at least one surface of the polydimethylsiloxane film is provided with patterns, the sizes of the patterns are between 0.1 and 500 µm, and the unit amount of the patterns in a square centimeter is between 1 and $10^{12}$.

Preferably, the non-planar structure is formed on the flexible substrates provided with patterned surface, and the patterns are formed by coating the polydimethylsiloxane onto a template and solidifying it.

The template is anyone of a silicon substrate provided with microstructure, a glass substrate provided with microstructure, a metallic substrate provided with microstructure, a plastic substrate, fabric or silk article provided with microstructure, and a bio-organ provided with microstructure.

Furthermore, the conductive layer is attached with organic polymer material on the surfaces, wherein the organic polymer material is one or a combination of more of the follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), PDMS, and high-polymer rubber materials.

In order to achieve the above goal, the present invention also provides a preparation method of the piezoresistive electronic skin, comprising steps as follows:

S1. Preparing two patterned flexible substrates;

S2. Preparing a solution for the conductive layers, respectively coating it to the patterned surfaces of the two flexible substrates to form the conductive layers, assembling the conductive layers by making the patterned surfaces face to face to form a film device with the conductive layers being contacted with each other;

S3. Forming upper, lower conductive electrodes respectively on the two conductive layers by the conductive material and leading wires from the conductive electrodes, thereby obtaining a piezoresistive electronic skin. Preferably, the solution for the conductive layer is a solution of carbon nanotubes, and the conductive layer is a carbon nanotube film.

Compared with the existing technologies, the present invention has advantages as follows: the piezoresistive electronic skin uses carbon nanotube films as the conductive layers and uses materials, such as polydimethylsiloxane, polyethylene terephthalate, polyvinyl alcohol, polyvinyl formal, polyethylene, and so on, as the flexible substrates, allowing the substrate to be high flexible and pliable, and to have low operating voltage, little power consumption, as well as high sensitivity and short response time. Employing the patterned flexible substrate with the increased amount of contact resistances as the basis greatly improves the sensitivity of electronic skin reacting to tiny applied force from the outside. Meanwhile, the template used in the patterning process is a soft template, such as fabric, silk cloth, and the like, which has low-cost, is easy to get, and does not need any complex micromachining process, effectively improving the practicality of the technical solution, saving material resources and decreasing the manufacturing cost of the piezoresistive electronic skin.

Another goal of the present invention is to provide a capacitive electronic skin and the preparation method thereof, which provides a solution to solve the existing problems of high working voltage, high power consumption and low sensitivity.

In order to achieve the above goal, the present invention provides a technical solution as follows:

A capacitive electronic skin, comprising a flexible sensitive layer, at least one of an upper surface and a lower surface of the sensitive layer having non-planar structure; and an upper electrode layer and a lower electrode layer respectively formed on the upper surface and the lower surface of the sensitive layer. Preferably, at least one of the upper surface and the lower surface of the upper electrode layer has non-planar structure, and/or at least one of the upper surface and the lower surface of the lower electrode layer has non-planar structure.

Further, at least one surface of the sensitive layer has patterns, and the patterns are formed by coating the polydimethylsiloxane onto a template.

The template is anyone of a silicon substrate provided with microstructure, a glass substrate provided with microstructure, a metallic substrate provided with microstructure, a plastic substrate, fabric or silk article provided with microstructure, and a bio-organ provided with microstructure.

Preferably, the material of the sensitive layer is polydimethylsiloxane (PDMS), the thickness of which is in a range of 2-50 µm. Alternatively, the material of the sensitive layer is high molecular material, and the high molecular material is one or a combination of more of polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), and high-polymer rubber materials.

Accordingly, a preparation method of the capacitive electronic skin is provided, comprising steps as follows:

S1. Providing a template which is capable of being formed with the non-planar structure;

S2. Coating an organic molecular layer on the surface of the template;

S3. Forming a sensitive layer on the organic molecular layer;

S4. stripping the solidified sensitive layer from the template after heat-treating it;

S5. Coating an upper electrode layer and a lower electrode layer respectively on the upper surface and the lower surface of the sensitive layer.

Compared with the existing technologies, the present invention has advantages as follows: By incorporating new micro-nano sensing technology and using the ultrathin, elastic film material which is non-toxic and has good biocompatibility, the capacitive electronic skin of the present invention can be well attached to human skin to form a wearable device and provide excellent user experience. In the meantime, due to the distinctive nanostructure of the sensitive material, the device has high sensitivity, good stability and easy portability with light weight and small size.

The capacitive electronic skin of the present invention effectively avoids the problem of low carrier mobility, so it needs low working voltage (usually is 2V) and low power consumption, meanwhile, the device has high sensitivity due to its distinctive microstructure.

The present invention also provides a use of the piezoresistive electronic skin and the capacitive electronic skin in detecting human pulse, cardiac pulsation, tension, breathing, intraocular pressure, vibration of muscle groups in the throat, speech recognition, muscle and skin movement caused by moving, blood pressure, and in medical robot, endoscopic robot system, surgery mechanical arm on the aspect of touching, sensing and protecting human organ.

Another goal of the present invention is to provide a speech recognition system and a method respectively on the basis of the piezoresistive electronic skin or the capacitive electronic skin so as to solve the problems of poor speech input effect and low recognition rate in the existing technology.

In order to achieve the above goal, technical solutions are provided as follows:

A speech recognition system is provided, which comprises:

the above-mentioned piezoresistive electronic skin, comprising: a plurality of overlapped flexible substrates; a conductive layer arranged on contact surface of adjacent flexible substrates, at least one contact area of the conductive layer having non-planar structure; and conductive electrodes electrically connected with the conductive layer;

a data processing module for receiving signals from the piezoresistive electronic skin and transmitting the processed signals to display module;

a display module for receiving and displaying the signals from the data processing module.

Another speech recognition system is also provided, which comprises:

a capacitive electronic skin, comprising: a flexible sensitive layer, at least one of an upper surface and a lower surface of the sensitive layer having non-planar structure; and an upper electrode layer and a lower electrode layer respectively formed on the upper surface and the lower surface of the sensitive layer;

a data processing module for receiving signals from the capacitive electronic skin and transmitting the processed signals to display module;

a display module for receiving and displaying the signals from the data processing module.

The present invention also provides a speech recognition method, comprising steps as follows:

collecting vibration signals of vocal cords by means of the above-mentioned piezoresistive electronic skin or collecting vibration signals of vocal cords by means of the capacitive electronic skin;

filtering and amplifying the collected vibration signals, and extracting characteristic signals;

analyzing and recognizing the characteristic signals by time domain analysis method or frequency domain analysis method, and displaying the recognition results by means of a display module.

Another goal of the present invention is to provide a pulse detection system and a method respectively on the basis of the piezoresistive electronic skin or the capacitive electronic skin so as to solve the existing technical problems of the pulse detection device, such as big size, high energy consumption, low accuracy, high cost, disability of displaying a full waveform of pulse wave, etc.

In order to achieve the above goal, technical solutions are provided as follows:

A pulse detection system is provided, comprising:

the piezoresistive electronic skin according to anyone of the above; or, the capacitive electronic skin according to anyone of the above;

a filter circuit for filtering the signals received from the piezoresistive electronic skin or the capacitive electronic skin to obtain valid pulse signals;

an amplification circuit for amplifying the valid pulse signals and transmitting them to an analog-to-digital conversion circuit;

a display device for receiving and displaying the signals received from the analog-to-digital conversion circuit.

Preferably, the analog-to-digital conversion circuit communicates with the display device by BLUETOOTH (a trademark), ZIGBEE (a trademark) or WIFI (a trademark).

A pulse detection method is also provided, comprising steps as follows:

collecting pulse signals by means of the above-mentioned piezoresistive electronic skin or the above-mentioned capacitive electronic skin;

filtering the collected pulse signals to obtain valid pulse signals;

amplifying the valid pulse signals and transmitting them to an analog-to-digital conversion circuit;

displaying the signals received from the analog-to-digital conversion circuit by means of a displayer.

Compared with the existing technologies, the present invention has advantages as follows:

By incorporating new micro-nano sensing technology and using the ultrathin, elastic film material which is non-toxic and has good biocompatibility, the piezoresistive electronic skin or the capacitive electronic skin can be well adhered to human skin to form a wearable device and provide excellent user experience. In the meantime, due to the distinctive nanostructure of the sensitive material, the device has high sensitivity, good stability and portability with light weight and small size as well as low cost. Furthermore, the speech recognition system and method obtained on the basis of the above-mentioned piezoresistive electronic skin or the capacitive electronic skin solve the existing technical problems of poor speech detection effect and low recognition rate, having property of synchronized reorganization, high recognition rate, small size and being convenient to carry. Moreover, the pulse detection system and method obtained on the basis of the piezoresistive electronic skin or the capacitive electronic skin solve the existing problems, such as big size, uncomfortable experience during pressurization and depressurization, low accuracy in the pulse detection, disability of displaying a full waveform of pulse wave, high cost, and so on, having high sensitivity, good stability, low energy consumption, being light, small and wearable.

BRIEF DESCRIPTION OF THE DRAWINGS

FIG. 1 is a schematic diagram of a piezoresistive electronic skin according to a preferred embodiment of the present invention;

FIG. 2 is a flow diagram of a preparation method of an electronic skin according to an embodiment of the present invention;

DETAILED DESCRIPTION OF ILLUSTRATED EMBODIMENTS

Figure 3:
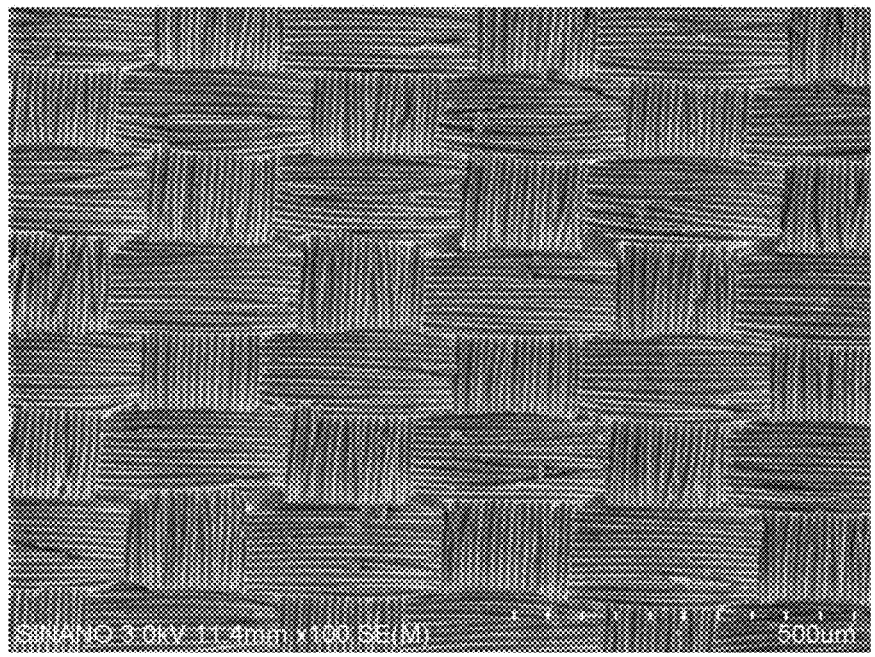
FIG. 3 is a SEM image of a polydimethylsiloxane film provided with micropattern according to an embodiment of the invention.

The present invention will be further explained below in detail with reference to figures and particular embodiments.

Embodiment 1

This embodiment provides a piezoresistive electronic skin, comprising: a plurality of overlapped flexible substrates; a conductive layer arranged on contact surface of adjacent flexible substrates, at least one contact area of the conductive layer has non-planar structure; and conductive electrodes electrically connected with the conductive layer.

Referring to FIG. 1, as an embodiment, the electronic skin comprises two flexible substrates 11, 12; two conductive layers 21, 22 respectively coated on the two flexible substrates 11, 12, the two conductive layers 21, 22 are contacted with each other; two conductive electrodes 31, 32 respectively contacted with the two conductive layers 21, 22.

In specific implementations, each of the flexible substrates is made of various materials.

In another embodiment, at least one of the flexible substrates uses a polydimethylsiloxane film, at least one surface of the polydimethylsiloxane film is provided with micro-nano patterns, the sizes of the patterns are between 0.1 and 500 μm, and the unit amount of the patterns in a square centimeter is between 1 and $10^{12}$. In another embodiment, at least one of the flexible substrates is made of one or a combination of more of the follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), and high-polymer rubber materials.

In the present embodiment, the patterns are preferably formed by coating the polydimethylsiloxane onto a template and solidifying it. Particularly, for example, degassing it in vacuum for 1-30 minutes and coating it onto a template. The template is preferably anyone of a silicon substrate provided with microstructure, a glass substrate provided with microstructure, a metallic substrate provided with microstructure, a plastic substrate, fabric or silk article provided with microstructure, and a bio-organ provided with microstructure. In specific implementations, making a template by material which is easy to get will effectively improve the practicality of the piezoresistive electronic skin and greatly decrease the manufacturing cost of the piezoresistive electronic skin.

The conductive layers 21, 22 comprise a carbon nanotube film which comprises networks formed by cross-linked carbon nanotubes. The light transmittance of the carbon nanotube film is between 50% and 97%, and the sheet resistance of the carbon nanotube film is between $10^2$ Ω/sq and $10^7$ Ω/sq. The thickness of the carbon nanotube film is approximately between 10 nm and 500 nm. The carbon nanotube film is made of one type or a combination of more types of single-walled carbon nanotubes, double-walled carbon nanotubes and multi-walled carbon nanotubes, wherein the single-walled carbon nanotubes may be metallic single-walled carbon nanotubes, semiconductor-type carbon nanotubes or hybrid single-walled carbon nanotubes containing both metallic single-walled carbon nanotubes and semiconductor-type carbon nanotubes.

The carbon nanotube film may also be a carbon nanotube film mixed or modified by nitrogen or boron, precious metal, metal, surface active agent, organic macromolecule compound, and so on. The carbon nanotubes may be carbon nanotubes functionalized by hydroxy (—OH), carboxyl (—COOH), amidogen (—$NH_2$), by high molecular polymer, by metal nanoparticle, by metallic oxide, or by biomolecule.

The conductive layers 21, 22 may also be made of one or a combination of more of any conductive metal among copper, silver and gold, and semiconductor materials.

In another embodiment, the conductive layer is attached with organic polymer material on the surface.

Furthermore, analogized with the material of the flexible substrates, the organic polymer material is preferably likewise one or a combination of more of the follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), polydimethylsiloxane (PDMS), and high-polymer rubber materials. Thereinto, the high-polymer rubber materials include, but are not limited to, butyl rubber, cis-polybutadiene rubber, chloroprene rubber, ethylene propylene diene monomer rubber, acrylate rubber, and polyurethane rubber. In the present embodiment, the sensitivity and stability of the conductive layer can be increased by adhering different materials to the surface of the conductive layer.

Preferably, in one embodiment, a layer of PVDF piezoelectric material (not limited to PVDF) may be added between the conductive film layers 21, 22 shown in FIG. 1, so as to improve the sensitivity and stability of the device.

In the embodiment as shown in FIG. 1, the conductive electrode 31 is connected with the conductive layer 21 but is not connected with the conductive layer 22, while the conductive electrode 32 is connected with the conductive layer 22 but is not connected with the conductive layer 21, and the thin film of carbon tubes provided with micro-nano patterns can only be connected with one of the conductive electrodes, respectively. Moreover, the conductive electrodes 31, 32 are made of any material or a combination of more materials of gold, platinum, nickel, silver, indium, copper, carbon nanotube and graphene.

In the present embodiment, the way the two layers of patterned conductive films are assembled, that is, the way the device is packaged, makes a big impact on the stability of the device. Thereinto, in one embodiment, the device is packaged by adhering the two layers of films from periphery and surroundings to form a stable quasi-single layer structure.

Embodiment 2

Referring to FIG. 2, the present invention also provides a preparation method of the piezoresistive electronic skin, the steps are as follows:

S1. Preparing two patterned flexible substrates, at least one layer of which is polydimethylsiloxane film.

In the step S1, the polydimethylsiloxane film is prepared by the following method, comprising a step S11 and a step S12:

S11. Degassing polydimethylsiloxane in vacuum for 1-30 minutes and coating it onto a template provided with patterns, wherein the polydimethylsiloxane has a thickness of 0.1 mm to 3 mm, and then heating it for more than 0.5 hour at a temperature of 50☐ to 100☐ to solidify and mold it;

S12. Removing the solidified and molded polydimethylsiloxane from the template by ultrasound in organic solvent for 5 to 30 minutes.

In specific implementations, the template may be anyone of a silicon substrate, a glass substrate, a metallic substrate, a plastic substrate, fabric, silk article, each of which has microstructure, and a bio-organ provided with microstructure. The organic solvent may be methanol, ethyl alcohol or ethylene glycol. One or two surfaces of the prepared polydimethylsiloxane film are placed in the oxygen plasma condition to react for 1 to 60 minutes. The polydimethylsiloxane film may also be high molecular materials, including but not limited to one or a combination of more of the follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), PDMS, and high-polymer rubber materials. Thereinto, the high-polymer rubber materials include, but are not limited to, butyl rubber, cis-polybutadiene rubber, chloroprene rubber, ethylene propylene diene monomer rubber, acrylate rubber, and polyurethane rubber.

In the present embodiment, the density of the microstructure is $(X*Y)$ lines/cm$^2$, wherein $1<X<10^6$, $1<Y<10^6$. Thereinto, the density of the microstructure is defined as a density in a unit area of a square centimeter. The high-density structure refers to a structure with a density more than 44*77 lines/cm$^2$, while the low-density structure refers to a structure with a density less than 27*38 lines/cm$^2$. In the embodiment, the preferred density is 44*77 lines/cm$^2$. In theory, the higher density, the higher sensitivity.

In the present embodiment, with the use of the microstructure, the piezoresistive electronic skin has good output capability, wherein the sensitivity may reach up to 1.8 KPa$^{-1}$, the lower limit of detection may reach to 0.6 Pa, and the response time may reach to 10 ms. Referring to FIG. 3, it is a scanning electron microscope (SEM) image of the prepared polydimethylsiloxane film provided with micro-nano pattern, showing that the polydimethylsiloxane film is formed with periodic microstructure patterns thereon.

S2. Preparing a solution for the conductive layer. In one embodiment, the solution for the conductive layer is a solution of carbon nanotubes, and the conductive layer is preferably a carbon nanotube film. Coating it to the patterned surfaces of the two flexible substrates to form carbon nanotube films, respectively. Assembling the carbon nanotube films by making the patterned surfaces face to face to form a film device with carbon nanotube films being contacted with each other.

The step S2 may particularly comprise steps S21-S23:

S21. Adding single-walled carbon nanotubes and/or double-walled carbon nanotubes, few-walled carbon nanotubes, multi-walled carbon nanotubes into an aqueous solution containing 1 wt %-10 wt % of surfactant until the concentration of carbon nanotubes reaches to 0.01-50 mg/ml, then, pre-dispersing the mixed solution by ultrasound for 1 min-10 h to form carbon nanotube dispersion solution. In the present embodiment, the surfactant may be common ionic surfactant or non-ionic surfactant, preferably is ionic surfactant, more preferably, but is not limited to, sodium dodecylsulphate, sodium dodecyl benzene sulfonate and so on, with a preferred concentration of 1-10 wt %.

S22. Centrifuging the carbon nanotube dispersion solution at a speed of 1000-20000 rpm for more than 0.1 h, and taking the supernatant as pre-filmed solution.

S23. Diluting the pre-filmed solution for 1-100 times by deionized water, and then evenly spraying the diluted solution of carbon nanotubes to the patterned surfaces of the two flexible substrates by sprayer to form carbon nanotube films. Assembling the carbon nanotube films by making the patterned surfaces face to face to form a film device with carbon nanotube films being contacted with each other. It should be explained that, the thickness and the electrical conductivity of the carbon nanotube film depend on the amount of carbon nanotubes contained therein and the time of spraying. The more content of carbon nanotubes and time of spraying, the better strength and electrical conductivity. In the present embodiment, the film-forming process may be performed in common film-forming manners, such as by vacuum filtration or spin coating, spray coating, printing, etc. For example, if the film is formed by spray coating, the process is as follows in detail: spraying the diluted carbon nanotube dispersion solution to the patterned polydimethylsiloxane film at a pressure of 0.1-1 psi by sprayer, and then putting the film in heating furnace and heating it to 80-120° C. to speed up the evaporation of water, after that, washing off the residual surfactant in the carbon nanotube film by deionized water so as to form a carbon nanotube film coated on the patterned polydimethylsiloxane film. If the film is formed by printing, coating and so on, the process is as follows in detail: coating the diluted carbon nanotube dispersion solution, by spin coating, spray coating and so on, to the material having flat surface, such as glass, mica, silicon wafer, and the like, so as to form a film. Accordingly, a method for removing the base is as follows: steeping it in water or aqueous solution containing acid, alkali, salt and so on until the carbon nanotube film falls off from the base, then shifting the carbon nanotube film onto the patterned polydimethylsiloxane film.

Furthermore, before the assembling of the film device, step S23 comprises steeping the film which has the carbon nanotube film on the surface for several times by deionized water so as to remove the surfactant, disposing the carbon nanotube film in strong acid with a concentration of 3-8M for 0.1-24 h after drying it. In the present embodiment, the strong acid may be anyone or a combination of nitric acid and hydrochloric acid.

Figure 4:
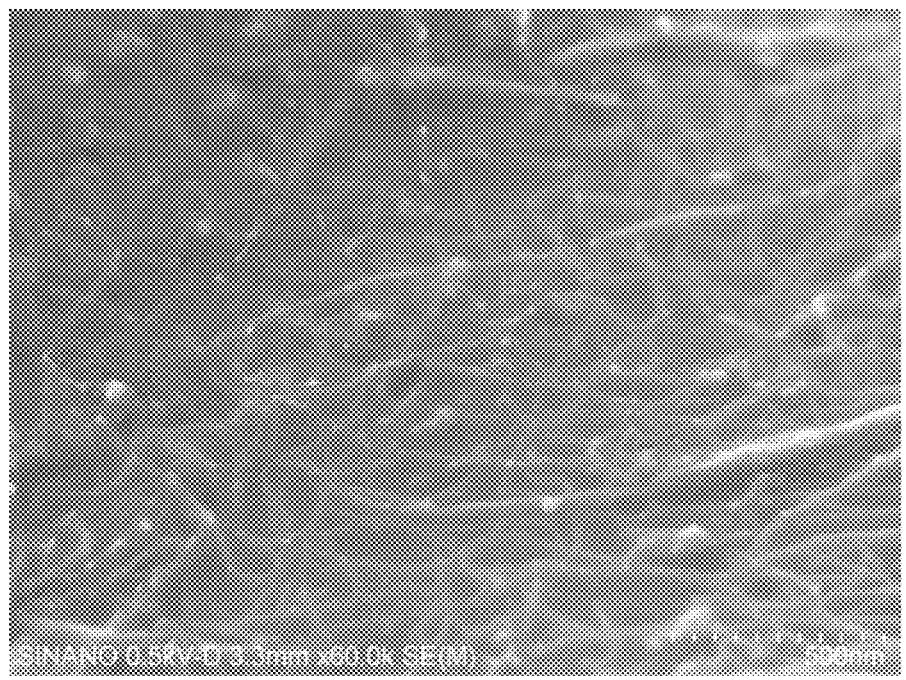
FIG. 4 is a SEM image of a single-walled carbon nanotube film according to an embodiment of the invention.

Referring to FIG. 4, it is a SEM image with single-walled carbon nanotubes affixed to the polydimethylsiloxane film, showing that single-walled carbon nanotubes are cross-linked with each other and are affixed to the surface of the polydimethylsiloxane film.

S3. Forming upper, lower conductive electrodes respectively on the two carbon nanotube films by conductive material and leading wires from the conductive electrodes, thereby obtaining a piezoresistive electronic skin.

In the step S3, the conductive materials for electrodes may be silver paste or fulmargin, or may be gas electrode such as gold, silver, copper, aluminum, or the like, which is made by steaming, ion sputtering and so on.

Figure 5:
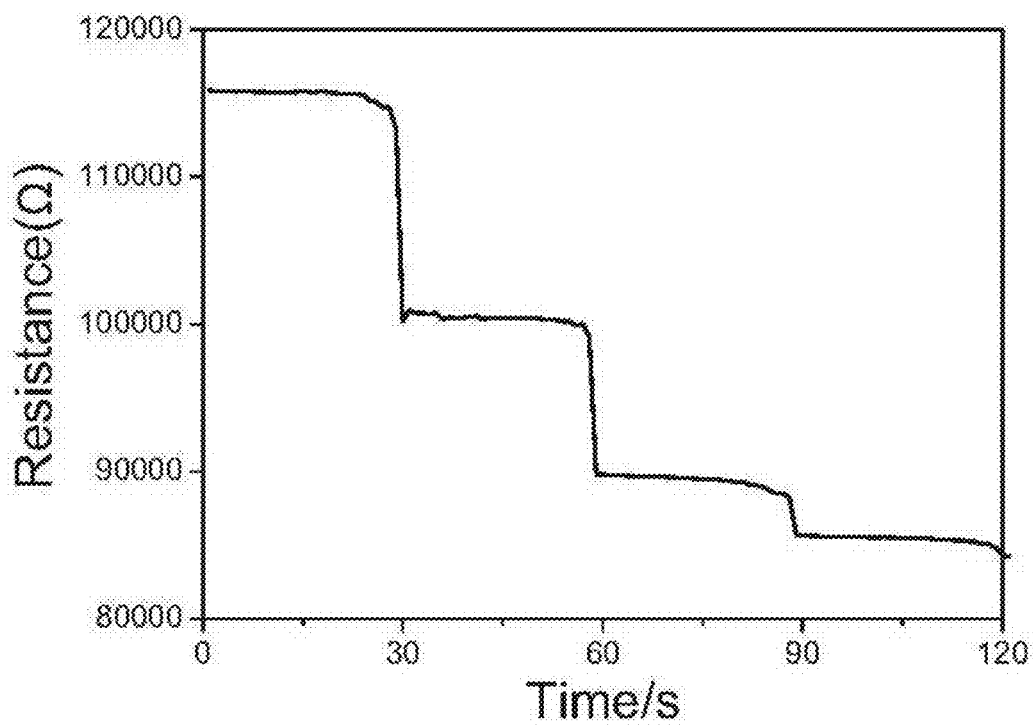
FIG. 5 is a plot of resistance versus the change of pressure using an electronic skin according to an embodiment of the present invention.

Referring to FIG. 5, at an operating voltage of 1V and in air atmosphere, the resistance value of the piezoresistive sensor is measured as 110-120 kΩ. At time points of 30 seconds, 60 seconds, 90 seconds, the resistance values are decreased fast when pressures of 60 Pa, 120 Pa and 180 Pa are accordingly applied respectively. For example, when a pressure of 60 Pa is applied, the resistance value is rapidly decreased to 95-105 kΩ. The result indicates that the piezoresistive sensor has high sensitivity and very short response time.

Compared with the existing technologies, the present invention has advantages as follows: the piezoresistive electronic skin uses carbon nanotube film as the conductive layer and uses materials, such as polydimethylsiloxane, polyethylene terephthalate, polyvinyl alcohol, polyvinyl formal, polyethylene, and so on, as the flexible substrates, enabling the substrate has advantages of high flexibility and being pliable, and it needs low operating voltage and little power consumption, but has high sensitivity and short response time. Moreover, the electronic skin uses the micro-patterned flexible substrate as the basis, with increased amount of contact resistances and obtains improved sensitivity to tiny applied force from the outside. Meanwhile, the template used in the patterning process is a soft template, such as fabric, silk cloth, and the like, which has low-cost and is easy to get, does not need any complex micromachining process, effectively improving the practicality of the piezoresistive electronic skin and greatly decreasing the manufacturing cost of the piezoresistive electronic skin.

Embodiment 3

Figure 6:
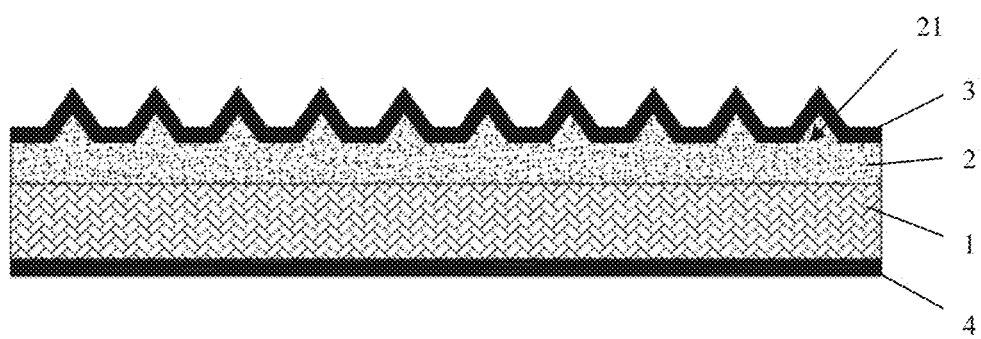
FIG. 6 is a schematic diagram of a capacitive electronic skin according to an embodiment of the present invention.

Referring to FIG. 6, the present embodiment provides a capacitive electronic skin.

In this embodiment, the capacitive electronic skin comprises a flexible support layer 1, a flexible sensitive layer 2 formed on an upper surface of the support layer 1, and an upper electrode layer 3 and a lower electrode layer 4 respectively formed on an upper surface of the sensitive layer 2 and a lower surface of the support layer 1. Preferably, the electrodes of the upper electrode layer 3 and the lower electrode layer 4 are formed by evaporation, sputtering or chemical deposition.

The material of the sensitive layer 2 is preferably PDMS (polydimethylsiloxane), while it may also be one or a combination of more of other high molecular materials, such as polyvinylidene fluoride (PVDF), polyvinyl fluoride (PVF), polyvinyl chloride (PVC), polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), and high-polymer rubber materials.

At least one of the upper surface and the lower surface of the sensitive layer 2 has non-planar structure. Furthermore, at least one of the upper surface and the lower surface of the upper electrode layer 3 has non-planar structure, and/or at least one of the upper surface and the lower surface of the lower electrode layer 4 has non-planar structure.

In one embodiment, the upper surface of the sensitive layer 2 has non-planar structure, preferably with a plurality of bulging and extending multi-cones 21. The bottom of each multi-cone 21 is a square with a side length 10 μm, the angle between side face and the bottom is 54.7°, and the multi-cone is 7.06 μm high.

In another embodiment, the upper surface of the sensitive layer 2 may have a shape of other non-planar structures such as wave and the like.

Obviously, the lower surface of the sensitive layer 2 may also have non-planar shape. Accordingly, the lower surface of the sensitive layer 2 should also be arranged with an electrode layer.

In specific implementations, at least one surface of the sensitive layer 2 has patterns, and the patterns are formed by coating the polydimethylsiloxane onto a template. The template is anyone of a silicon substrate provided with microstructure, a glass substrate provided with microstructure, a metallic substrate provided with microstructure, a plastic substrate, fabric or silk article provided with microstructure, and a bio-organ provided with microstructure.

In an embodiment, the support layer 1 is an ultrathin PE (polyethylene) film with high transparency and high flexibility, which preferably has a thickness of 12 μm.

The PE film is to help to readily separate the patterned PDMS film on the surface of the silicon wafer from the template integrally, and meanwhile it serves as a substrate to support the PDMS film. In addition, the support layer may be made of one or a combination of high-transparency, high-flexibility polyvinyl chloride (PVC) film and polyvinylidene chloride (PVDC) film.

The material of the upper electrode layer 3 and the lower electrode layer 4 is one or a combination of gold, platinum, nickel, silver, indium, copper, carbon nanotube, graphene, and silver nanowire.

With respect to the above electronic skin, the entire thickness of the support layer 1 and the sensitive layer 2 is less than 70 μm. The ultrathin electronic skin can function as a wearable device with the same softness with human skin, and it has light weight and can be adhered to skin directly.

Embodiment 4

An embodiment of the present invention provides a preparation method of the capacitive electronic skin as follow:

S1. Preparing a template which is capable of being formed with non-planar structure;

In one embodiment, a template provided with microstructure (preferably a four-inch silicon wafer) is provided by processes such as lithography, etching, and so on in MEMS machining technology. At first, cleaning the surface of the silicon wafer, then spin coating with a photoresist, prebaking, performing photoetching, developing, postbaking, and finally shifting the patterning to the silicon wafer by etching, thereby forming a template provided with microstructure. The detailed preparation method is as follows:

1. Making Template

Drawing drawings by means of mapping software after the design is demonstrated. The simply increasing of both width and height of the pattern helps to improve the sensitivity of the device. After comprehensive analysis, in one embodiment, the micro-pattern has pyramid structure, the bottom of which is a square with a side length 10 μm, the angle between side face and the bottom is 54.7°, and the height from the top of the pyramid to the bottom is 7.06 μm. Making a mask plate according to the drawing size.

2. Preparing a Four-Inch Silicon Wafer

Single-side polishing a four-inch silicon wafer, and forming a 300 nm SiO2 layer on the polished single-side by thermal oxidation. Performing ultrasound respectively by MOS acetone and deionized water for 15 minutes, and then performing ultrasound by MOS ethyl alcohol for 10 minutes and drying it. After that, stoving at 105° C. for 10 minutes.

3. Patterning the Photoresist a. Whirl coating: spin coating with 6-7 μm photoresist, preferably AZ4620, on the surface of the prepared four-inch silicon wafer, with a pre-speed 500 rpm for 6 s and a rotational speed of spin-coating 400 rpm for 30 s;

b. Prebaking: prebaking at 95° C. for 210 seconds;

c. Exposing: exposing for 24 s in low-vacuum mode by means of MA6 contact aligner;

d. Developing: the ratio of tetramethylammonium hydroxide to deionized water of the developing solution is 1:8, and the developing time is 95 s;

e. Postbaking at 95° C. for 180 seconds.

Figure 7:
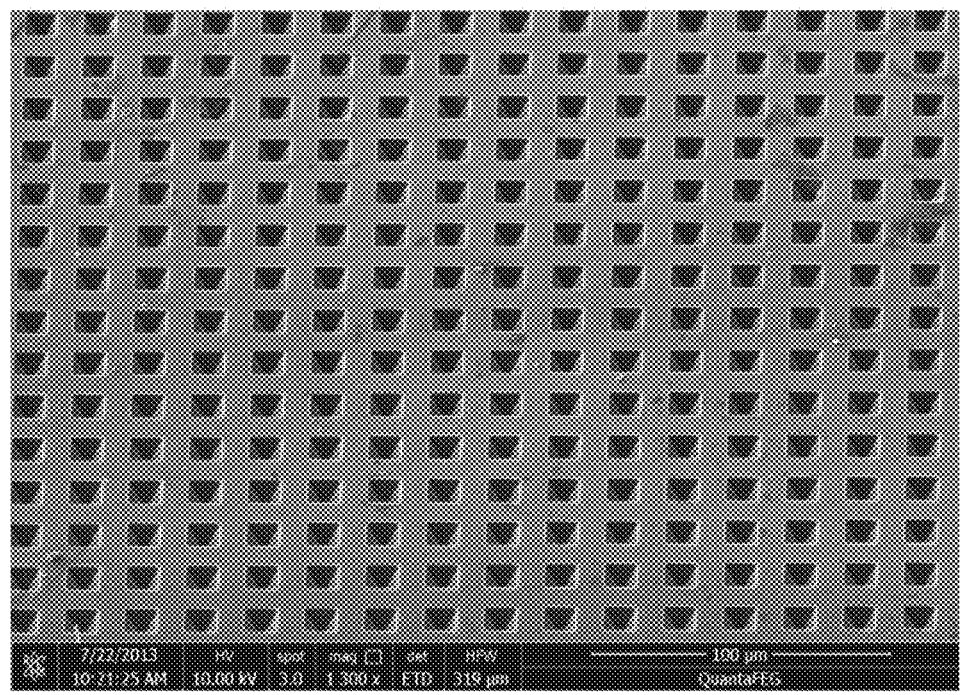
FIG. 7 is a SEM image of a silicon wafer template according to an embodiment of the present invention.

4. Shifting the Patterning to the Silicon Wafer a. Removing the photoresist: by means of plasma stripper, removing the photoresist coating remained after being developed;

b. Dry etching: removing the patterned SiO2 layer by reactive ion etching (RIE), for 6 minutes;

c. Directional wet etching: etching by 30% KOH solution at 78° C. for 9 minutes, and finally forming a reverse rectangular cone structure on the surface of the silicon wafer, as shown in FIG. 7.

S2. Forming an organic molecular layer on the surface of the template

Processing (such as by vapor deposition or fume coating) a thin organic (trimethylchlorosilane or perfluorooctyl trichlorosilane) molecular layer on the surface of the template, so as to make sure that PDMS film on the surface of the silicon wafer can be separated from the template integrally and readily.

S3. Forming a sensitive layer on the organic molecular layer

Then, spin coating (the preferred rotation rate is 3000 r/min, for 30 s) a transparent liquid high polymer material (such as polydimethylsiloxane, with a preferred mass ratio of initiator to reactant being 1:10) on the organic molecular layer to form a very thin (the preferred thickness is 50 μm) and uniform film.

In another embodiment, after the step S3, coating a support layer on the sensitive layer, and then disposing the lower electrode plate on the lower surface of the support layer. Forming a layer of high-transparency, high-flexibility ultrathin PE (polyethylene) film (preferably with a thickness of 12 μm) on the surface of the above-mentioned film without gap and bubble (the layer may also have bubbles and gaps).

Figure 8:
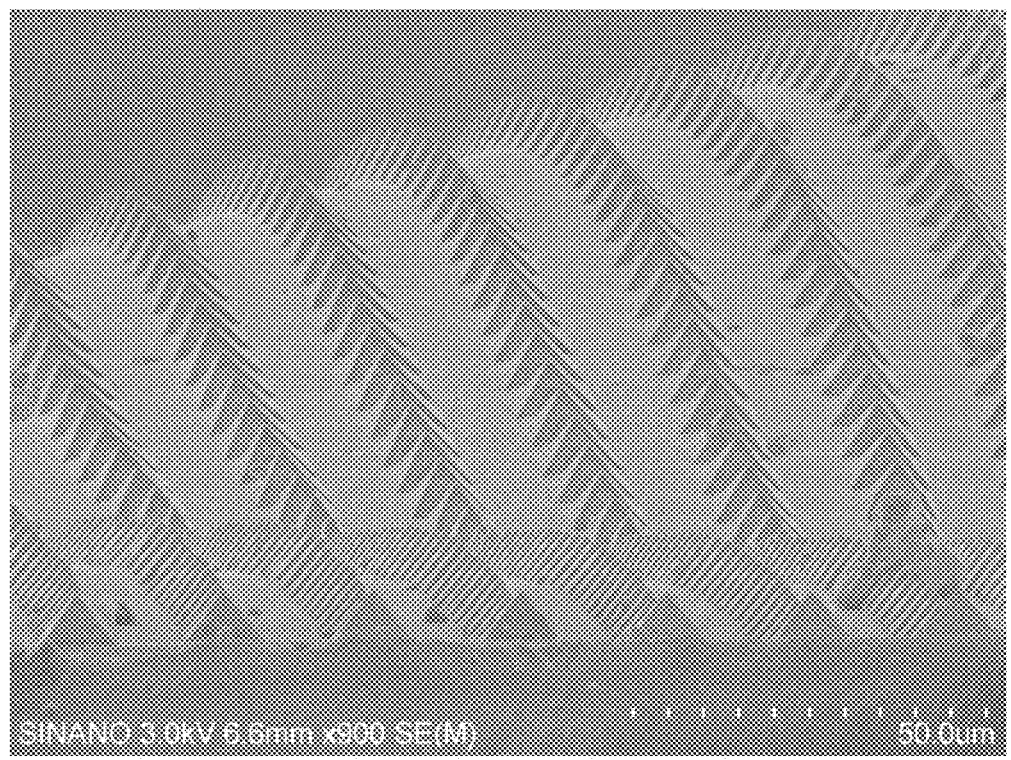
FIG. 8 is a SEM image of a flexible PDMS film molded from the template corresponding to FIG. 7.

S4. Heat-treating, and stripping the solidified sensitive layer and support layer from the template Heating in a vacuum environment (preferably at a temperature of 65-75 □) for a period of time (preferably 2-3 h), until the liquid high polymer PDMS film has been solidified completely. In another embodiment in which the support layer is provided, the PDMS layer is fully integrated with the PE film in the meantime. Then, stripping the solidified high polymer film from the surface of the silicon wafer template, thereby molding the micropattern of the silicon wafer template to flexible PDMS film and forming a film provided with pyramid micro-structure. The entire thickness of the film is less than 70 μm, as shown in FIG. 8.

S5. Forming an upper electrode layer and a lower electrode layer respectively on the upper surface and the lower surface of the sensitive layer Finally, evenly coating (such as by evaporation, chemical deposition and so on, preferably by evaporation) a layer of ultrathin nano conductive film (preferably coating Au conductive film with a thickness of 100 nm by evaporating Au particles with a purity of 99.9999%) respectively on the upper and lower surface of the film, thereby forming an ultrathin, flexible conductive electronic skin with lots of sensitive spots.

Then, respectively leading-out (such as by viscosity-pressure, welding and so on, preferably by viscosity-pressure) a flexible electrode from Au nano conductive layer on the upper and lower surfaces of the ultrathin and flexible conductive electronic skin. The flexible electrode, for example, may be an enameled wire with a diameter of 0.1 mm, a flat copper foil tape with a thickness of 20 μm and with pressure-sensitive adhesive, or a flexible ultrathin copper foil with a thickness of 10 μm. Preferably, the flexible electrode is a flexible, ultrathin copper foil.

Finally, spin coating (preferably at a rotational speed of 5000 r/min, for 30 s) a layer of PDMS, so as to evenly form a very thin (the thickness is less than 10 μm) protective layer for the Au conductive layer, thereby forming an ultrathin, flexible capacitive electronic skin.

In another embodiment, forming a sensitive layer on the lower surface of the lower electrode layer after the step S5.

In the present embodiment, the template may be anyone of a silicon substrate, a glass substrate, a metallic substrate, fabric, silk article provided with microstructure, and a bio-organ provided with microstructure. The organic solvent may be methanol, ethyl alcohol or ethylene glycol. One or two surfaces of the prepared polydimethylsiloxane film are placed in the condition of oxygen plasma for 1 to 60 minutes. The polydimethylsiloxane film may also be high molecular materials, including but not limited to one or a combination of more of polyethylene terephthalate, polyvinyl alcohol, polyvinyl formal and polyethylene.

Furthermore, in another embodiment, when the lower electrode layer is formed on the upper surface of the support layer, the process for preparing the electronic skin is as follows in detail:

S11-S13 are same with the step S1-S3 in the present embodiment and need not be repeated here;

S14. Forming Au electrode with a thickness of 200 nm on the high-transparency, high-flexibility ultrathin PE (polyethylene) film (preferably with a thickness of 12 μm) by ion sputtering.

S15. Adhering Au conductive surface of the PE film, on which the Au electrode is formed, to the liquid high polymer film material formed in the above-mentioned step S3. Heating in a vacuum environment (preferably at a temperature of 65-75 □) for a period of time (preferably 2-3 h), until the above-mentioned liquid high polymer PDMS film has been solidified completely and meanwhile has been fully integrated with the PE film. Then stripping the solidified high polymer film from the silicon wafer template, thereby molding the micropattern on the silicon wafer template to flexible PDMS film and forming a film provided with pyramid micro-structure.

S16. Forming upper electrode on the micro-structure surface of the PDMS film, and finally forming a flexible, ultrathin capacitive electronic skin.

Figure 9:
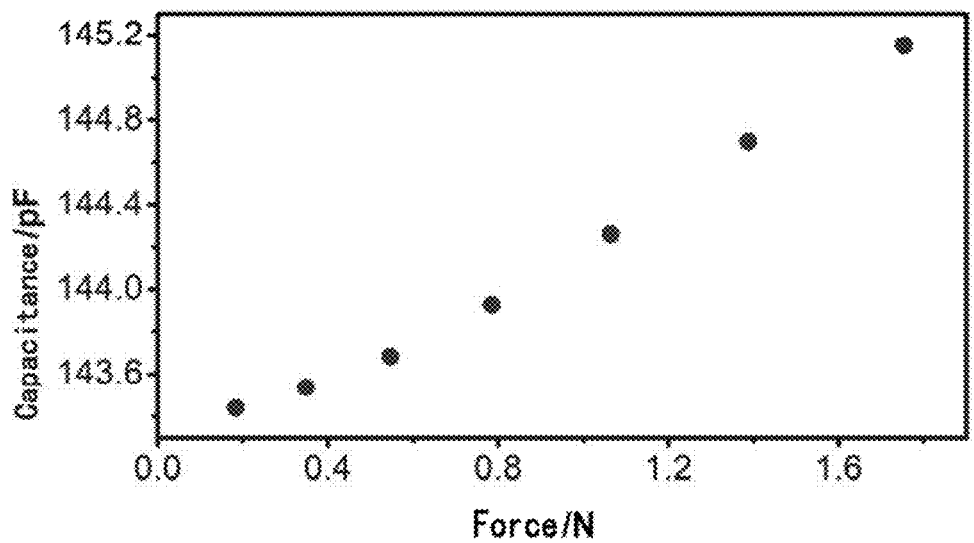
FIG. 9 is a plot of the response of a capacitive electronic skin versus applied force according to an embodiment of the present invention.

Referring to FIG. 9, it can be seen that the entire device is stretched under pressure, resulting in that the dielectric layer of the device gets thinner and bigger and capacitance gets bigger; and the entire device is contracted when the pressure is removed, resulting in that the dielectric layer of the device is recovered quickly and capacitance of the device gets smaller; thereby achieving high sensitivity measurement for pressure based on the present device with capacitor structure.

Embodiment 5

The international competition of information industry has been shown increasingly as the battle over science and technology. The speech recognition industry, as a strategic, forward-looking and important technology industry, has been the focus of scientific community and the industrial community. One embodiment of the present invention provides a new speech recognition technology and the relevant device. A simple, feasible and systematic method for recognizing vibration signals is also provided, comprising the steps as follows: collecting vibration signals generated by vocal cords during speaking by means of micro/nano sensor instead of collecting transmitted sound signals of voices in the air by means of acquisition module in traditional speech recognition technology, pre-treating the vibration signals, such as amplifying the vibration signals, filtering the vibration signals and the like, extracting characteristic signals, recognizing and analyzing by time domain analysis, frequency domain analysis and the like, and finally displaying the results.

This embodiment makes innovations on the basis of traditional speech recognition technology, mainly focused on the method for collecting speech signals and on the extracting device. It has advantages of synchronized recognition, high recognition rate, small size and being convenient to carry. In the meantime, due to the use of flexible thin film material, it's convenient to construct the present device as wearable equipment.

Figure 10:
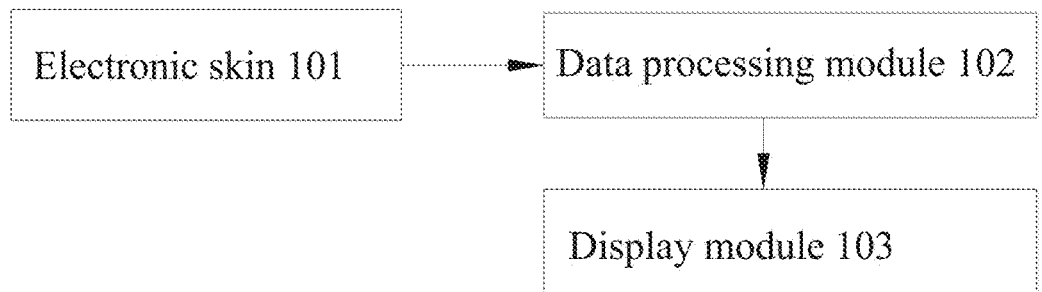
FIG. 10 is a schematic diagram of a speech recognition system according to an embodiment of the present invention.

As shown in FIG. 10, in an embodiment of the present invention, a speech recognition system comprises an electronic skin 101, a data processing module 102 and a display module 103. The electronic skin 101 includes piezoresistive electronic skin and capacitive electronic skin.

In this embodiment, the piezoresistive electronic skin or the capacitive electronic skin is used for collecting vibration signals of vocal cords, the data processing module 102 is used for filtering and amplifying the collected vibration signals, extracting characteristic signals, analyzing and recognizing the characteristic signals by time domain analysis method or frequency domain analysis method, and the display module 103 is used for displaying the recognition results.

In one embodiment, the piezoresistive electronic skin may be the piezoresistive electronic skin provided in the above embodiment 1, the detail structure of which refers to embodiment 1 and need not be repeated here. In another embodiment, the capacitive electronic skin may be the capacitive electronic skin provided in the above embodiment 3, the detail structure of which refers to embodiment 3 and need not be repeated here.

In addition, the preparation method of the piezoresistive electronic skin may take the preparation method of the piezoresistive electronic skin provided in the above embodiment 2 for reference; and the preparation method of the capacitive electronic skin may take the preparation method of the capacitive electronic skin provided in the above embodiment 4 for reference, both need not be repeated here.

In specific implementations, as to the capacitive electronic skin, when the device is put on the throat where vocal cords are, sensor capacitance changes due to vocal-cord vibration. Then filtering out the background noise signals by means of a filter in circuit to get valid pulse wave signals, amplifying the signals by amplifying circuit and transmitting the signals to the receiving device on the displayer by wireless BLUETOOTH (a trademark), ZIGBEE (a trademark) or WIFI (a trademark) transmitter technology, thereby synchronously displaying the vibration wave of vocal cords generated during speaking on the displayer.

Figure 11:
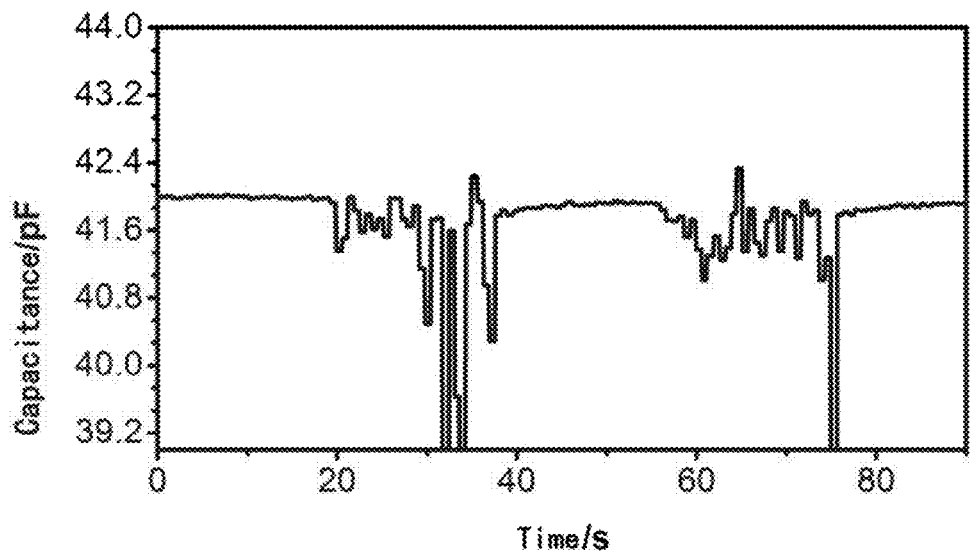
FIG. 11 is a plot showing the detection results of speech recognition with the use of a capacitive electronic skin according to an embodiment of the present invention.

When the device is attached to vocal cords area, during speaking, vocal cords accordingly vibrate, the vibration signals are automatically collected by sensors, switched and recognized by external circuits, transmitted to the displayer (preferably 7-inch pad) by BLUETOOTH (a trademark), and the amplitude and frequency of the waveform shown on the displayer change according to stress, sound duration and the like. When using a capacitive electronic skin to detect speech, the detection result of speech recognition is shown in FIG. 11. According to the detection results shown in FIG. 11, the capacitive electronic skin has high sensitivity for the speech, and the speech recognition system has a good recognition effect.

Embodiment 6

Another embodiment of the present invention provides a speech recognition method, comprising:

Collecting vibration signals of vocal cords by means of the piezoresistive electronic skin according to embodiment 1 or the capacitive electronic skin according to embodiment 3;

Filtering and amplifying the collected vibration signals, and extracting characteristic signals;

Analyzing and recognizing the characteristic signals by time domain analysis method or frequency domain analysis method, and displaying the recognition results by means of a display module.

In an embodiment, the speech recognition method provided in the present embodiment may use the speech recognition system according to embodiment 5 to detect signals. Due to the high sensitivity of the piezoresistive electronic skin and the capacitive electronic skin and the portability of the speech recognition system, the speech recognition method is feasible, practicable and efficient.

Embodiment 7

Figure 12:
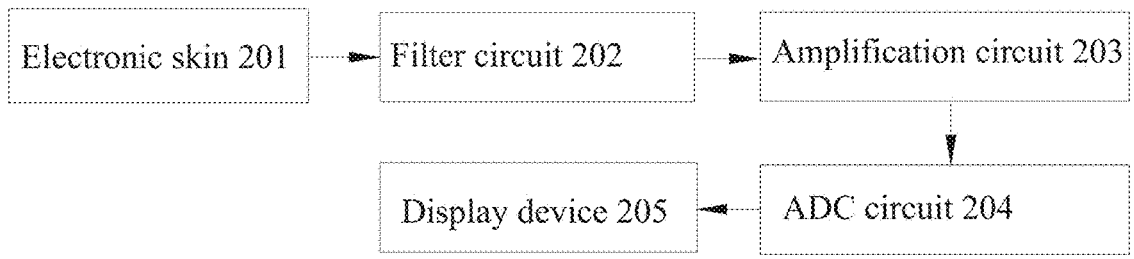
FIG. 12 is a schematic diagram of a pulse detection system according to an embodiment of the present invention.

Referring to FIG. 12, an embodiment of the present invention provides a pulse detection system.

The pulse detection system comprises an electronic skin 201, a filter circuit 202, an amplification circuit 203, an analog-to-digital conversion circuit 204 and a display device 205. In the present embodiment, the electronic skin 201 includes piezoresistive electronic skin and capacitive electronic skin.

Thereinto, the electronic skin in the present embodiment may be the piezoresistive electronic skin provided in embodiment 1 or the capacitive electronic skin provided in embodiment 3, the detail structures thereof refer to the above embodiments, and need not be repeated here.

Pulse is formed by the flow of the blood shot into aorta by ventricle and flowed along the arterial system from aorta root in the form of waves during the periodic expansion and contraction of the heart. When the above wearable pulse detection device is put on the area with aterial pulse, the signals of pulse pulsation with good integrality, small distortion, stable baseline and moderate amplitude are automatically collected by the piezoresistive electronic skin or the capacitive electronic skin, then the pulse signals output by the electronic skin are filtered out the background noise signals by means of the filter circuit 202 to get valid pulse wave signals, then the signals are amplified by an amplifying circuit and transmitted to an analog-to-digital conversion (ADC) circuit 203 (further comprises an analog-to-digital conversion circuit) to be switched, after that, the signals are transmitted to the receiving device on the display device 205 by wireless BLUETOOTH (a trademark) transmitting technology, ZIGBEE (a trademark) technology or WIFI (a trademark) technology, and finally the pulse waves are displayed on the displayer in real-time.

The analog-to-digital conversion circuit 204 and the display device 205 may communicate by GPRS (General Packet Radio Service), GSM (Global System of Mobile communication), WLAN (Wireless Local Area Networks), CDMA (Code Division Multiple Access), TDMA (Time Division Multiple Access), TV communication network, ZIGBEE (a trademark) technology or WIFI (a trademark) technology, or other telecommunication networks. Obviously, the analog-to-digital conversion circuit 204 and the display device 205 may also be connected in a wired manner.

In addition, the preparation method for the above piezoresistive electronic skin may refer to the preparation method for the piezoresistive electronic skin provided in the above embodiment 2, the preparation method for the above capacitive electronic skin may refer to the preparation method for the capacitive electronic skin provided in the above embodiment 4, and both need not be repeated here.

The pulse detection system provided in the present embodiment has advantages as follows: as the result of using the above piezoresistive electronic skin and capacitive electronic skin, it has advantages of toxic free and good biocompatibility. So it can be adhered to human skin and bring the user excellent experience. In the meantime, due to the distinctive nano structure of sensitive materials of electronic skin, the pulse detection system has high sensitivity and good stability, has portability as being light, small and flexible on the whole, and has low cost in fabrication, and thus it has good practicability.

Embodiment 8

An embodiment of the present invention provides a pulse detection method as follows:

Collecting pulse signals by means of the piezoresistive electronic skin according to the embodiment 1, or by means of the capacitive electronic skin according to the embodiment 3;

Filtering the collected pulse signals to get valid pulse signals;

Amplifying the valid pulse signals and transmitting them to an analog-to-digital conversion circuit;

Displaying the signals received from the analog-to-digital conversion circuit by means of a displayer.

In this embodiment, the pulse detection system according to embodiment 7 is used to detect pulse signals. When the device is put on the pulse, sensor capacitance changes with the beat of pulse. Then, filtering out the background noise signals by means of a filter circuit to get valid pulse wave signals, amplifying the signals by amplifying circuit and transmitting them to ADC circuit to be switched, transmitting the signals to a receiving device on a displayer by wireless BLUETOOTH (a trademark) transmitting technology, thereby displaying the pulse waves on the displayer in real-time.

Embodiment 9

An embodiment of the present invention provides multiple new uses of the electronic skin in a variety of fields.

The electronic skin provided in the present invention may be used for detecting human physiology signals comprising arterial pulsation, cardiac pulsation, tension detection, intraocular pressure, vibration of muscle groups in the throat caused by talking, speech recognition caused by contact and non-contact vibration, muscle and skin movement of other parts of the body caused by moving. For example, when detecting arterial pulsation at wrist, P-peak, T-peak and D-peak in the pulse can be accurately recognized. The arterial pulsation comprises the pulse in each part of the body beating with the arterial pulsation. Furthermore, the electronic skin has potential applications on the aspect of touching, sensing and protecting human organ, in respects such as blood pressure, breathing, medical robot, endoscopic robot system, surgery mechanical arm, etc.

In the present embodiment, the electronic skin comprises: the piezoresistive electronic skin according to embodiment 1 or the capacitive electronic skin according to embodiment 3, the detail structures thereof need not be repeated here.

New uses of the piezoresistive or capacitive electronic skin, in a variety of fields, provided by the present invention are explained by four particular embodiments as follows:

1) The Application of the Piezoresistive/Capacitive Electronic Skin on the Detection of Pulse Signals.

Figure 13:
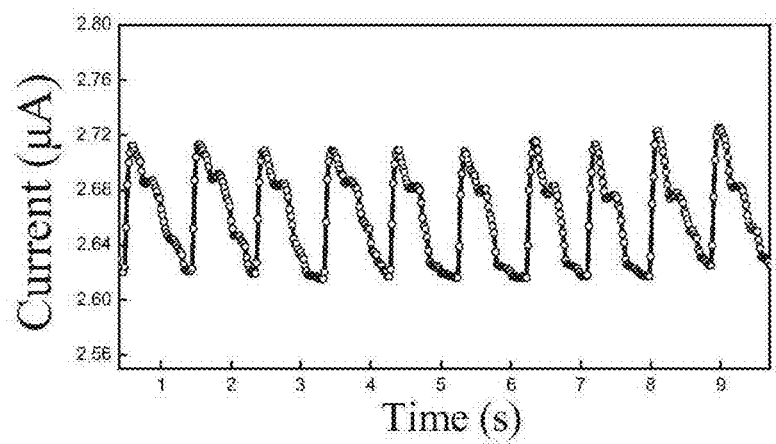
FIG. 13 is a oscillogram of a wrist pulse wave measured by a piezoresistive electronic skin according to an embodiment of the present invention.
Figure 14:
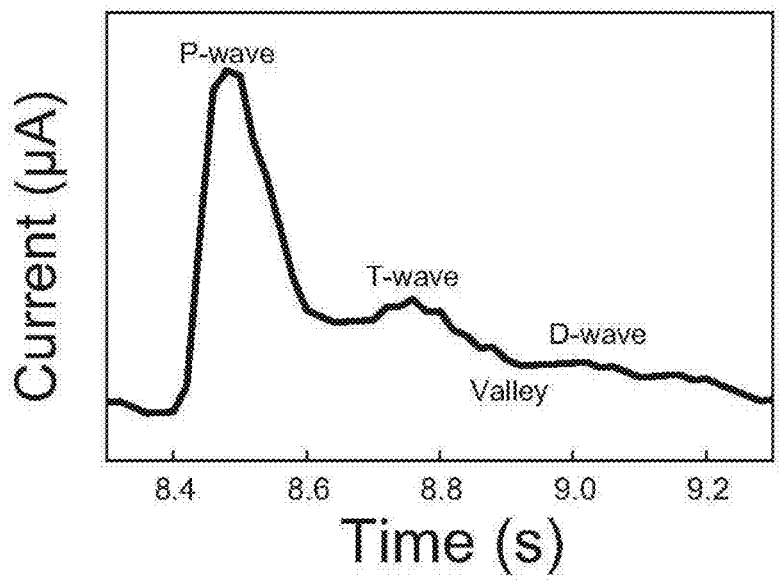
FIG. 14 is a oscillogram of an individual pulse waveform measured by a piezoresistive electronic skin according to an embodiment of the present invention.

Putting the prepared piezoresistive/capacitive electronic skin on the wrist, the detection of human pulse signals can be achieved by measuring current signals in real-time when the voltage is at 2V. Particularly, when using the piezoresistive electronic skin to detect an individual pulse wave, the oscillogram of wrist pulse measured by the piezoresistive electronic skin is shown in FIG. 13. FIG. 14 is a typical curve of a single waveform of the pulse wave measured by the piezoresistive electronic skin of the present invention. The result indicates that, the device not only achieves a quick and accurate real-time measurement of human pulse signals, but also may accurately distinguish P-peak, T-peak and D-peak in human pulse waves. Theses pulse waves are relevant to information of heart rate, cardiac pulsation, blood viscosity and the like of human body. By accurate detection of the pulse waves, previous diagnosis of human diseases may be achieved. The use of the device for measuring pulse at wrist is one embodiment, and the device may also be used for real-time measuring arterial pulsation at other parts of the body, such as at neck, head and the like.

2) The Application of the Piezoresistive/Capacitive Electronic Skin on Speech Recognition.

Figure 15:
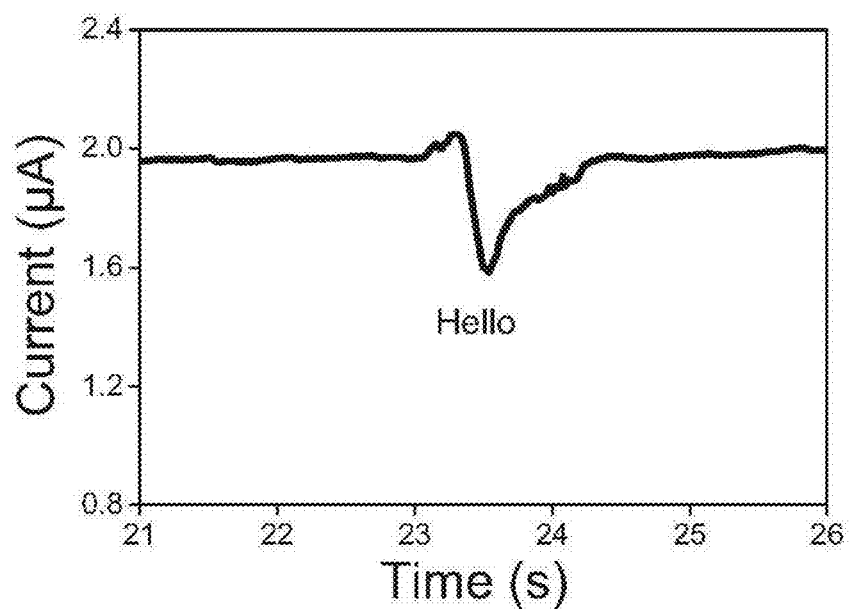
FIG. 15 is a first detection graph of speech recognition, with the use of a piezoresistive electronic skin according to an embodiment of the present invention.
Figure 16:
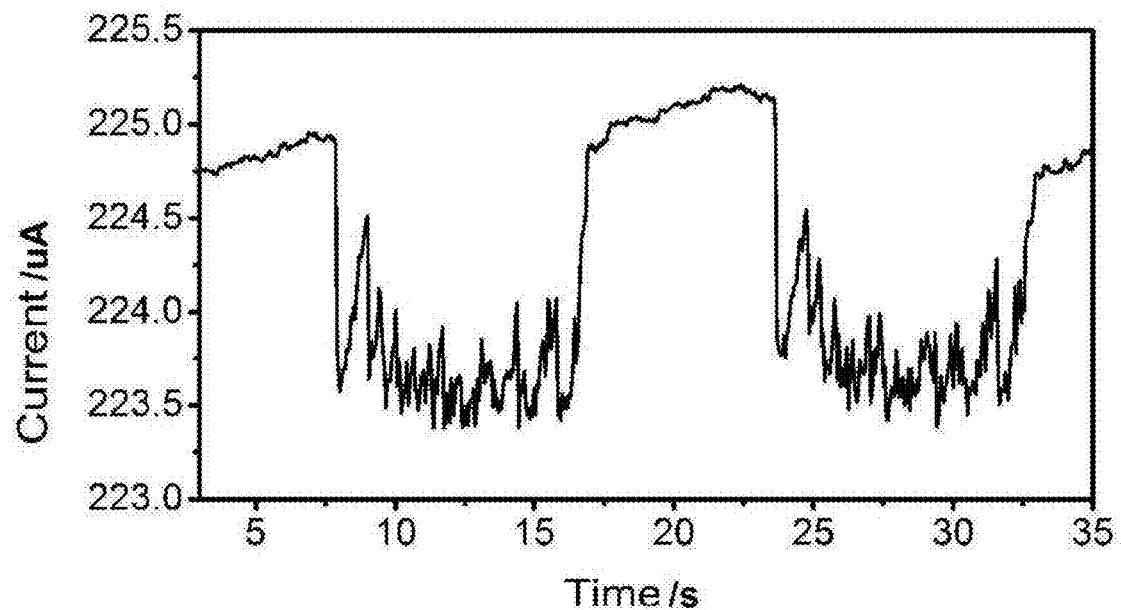
FIG. 16 is a second detection graph of speech recognition, with the use of a piezoresistive electronic skin according to an embodiment of the present invention.

Putting the prepared piezoresistive/capacitive electronic skin on neck, the recognition of human speech may be achieved by measuring current signals in real-time when the voltage is at 2V. In one embodiment, when using the piezoresistive electronic skin to detect speech, the real-time I-t curve obtained when a subject says hello is shown in FIG. 15. When the subject talks, the vibration of vocal cords may cause a vibration of skin, thereby resulting in that the resistance value of the device changes and the current flowed through the device also changes in the meantime. In this way, the relationship between speech and current is established. The waveforms of different speech and the changes thereof may be measured and obtained by the conversion of several physical quantities. Referring to FIG. 16, it is another detection graph of speech recognition, with the use of a piezoresistive electronic skin of the present invention. As shown in FIG. 16, when the piezoresistive electronic skin is put above a stereo without contact, the device vibrates in response to sound waves from the stereo. So the current value of the device changes. Besides, each type of sound vibration will have its own changing curve of current.

3) The Application of the Piezoresistive/Capacitive Electronic Skin on Tension Detection.

Figure 17:
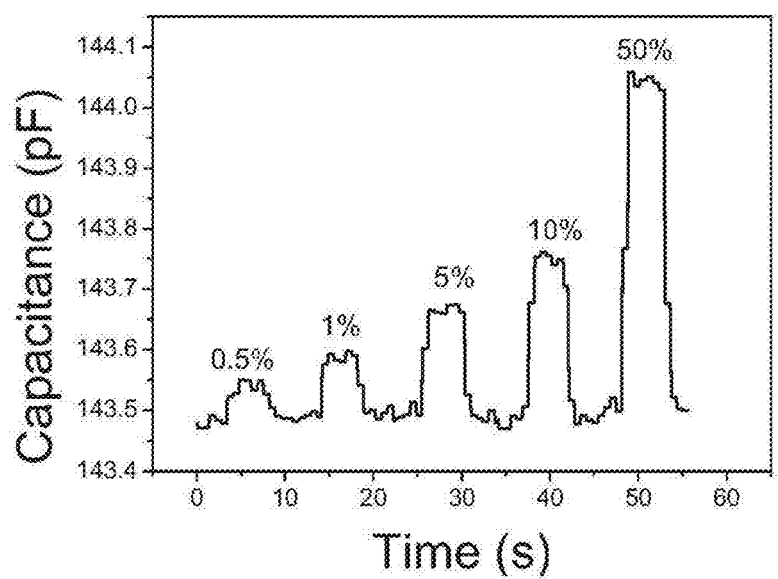
FIG. 17 is a response diagram of a capacitive electronic skin detecting external tension according to an embodiment of the invention.

The piezoresistive/capacitive electronic skin of the present invention may be applied to the detection of tension. In specific implementations, when the prepared piezoresistive/capacitive electronic skin is applied to the detection of tension, the deformation of the flexible piezoresistive/capacitive electronic skin caused under the outside tension is precisely controlled by a high-precision stepping platform. The dielectric thickness, electrode area and the structure of the piezoresistive/capacitive electronic skin change under the outside tension, and thus the resistance value or capacitance value of the electronic skin device changes. In one embodiment, when using the capacitive electronic skin to detect tension, a response diagram of the capacitive electronic skin detecting the external tension is obtained. As shown in FIG. 17, when the deformation quantity of the capacitive device is in a range of 0.5% to 50%, signal output with high sensitivity may be achieved. Due to the higher elasticity of PDMS, the detectable device deformation quantity of the piezoresistive/capacitive electronic skin is in a range of 0.01% to 200% when relevant materials are optimized.

4) The Application of the Piezoresistive/Capacitive Electronic Skin on Medical Robot System.

The electronic skin of the present invention may be applied on medical robot system and realizes functions of medical robot or surgery mechanical arm, touching, sensing and protecting human organ. Thereinto, the electronic skin includes the piezoresistive electronic skin and the capacitive electronic skin. Thereinto, the piezoresistive electronic skin has same structure with the piezoresistive electronic skin according to embodiment 1; the capacitive electronic skin has same structure with the capacitive electronic skin according to embodiment 3, and both need not be repeated here.

For example, applying the piezoresistive electronic skin to endoscopic robot and enabling the endoscopic robot to have ability to detect small applied force from outside. When performing endoscopic operation, the endoscopic robot system may obtain the touching signal of the human internal organ and input the information into the control center of the endoscopic robot system, and then the control center may adjust the postures and movements of the robot, reducing the pain of the patient and the damage for the human internal organ. In one embodiment, the piezoresistive electronic skin of the present invention may be applied on the self-guide endoscopic medical system.

Figure 18:
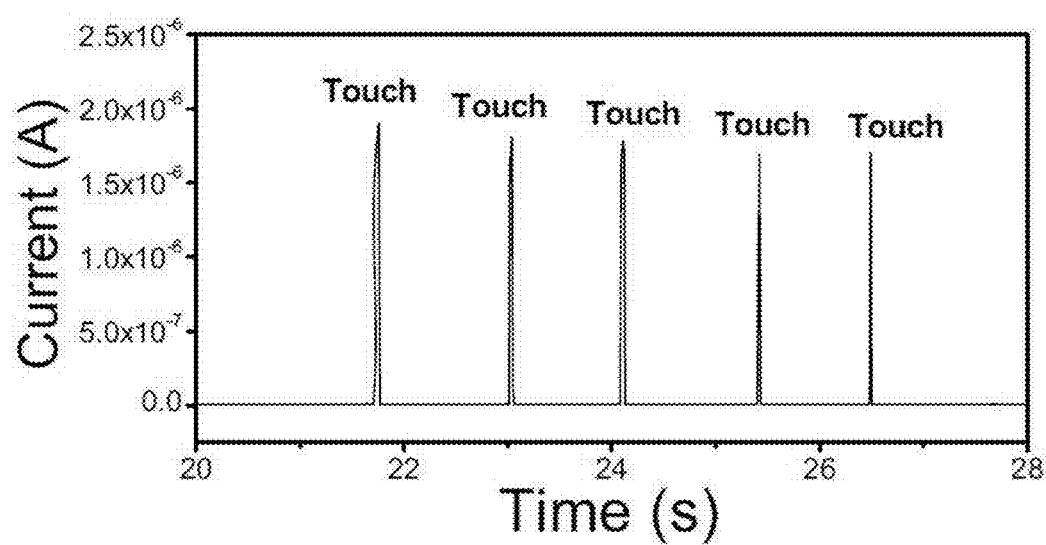
FIG. 18 is a force-signal acquisition graph of a piezoresistive electronic skin applied on the endoscopic medical system according to an embodiment of the invention.

Referring to FIG. 18, it is a signal acquisition graph of the endoscopic robot touching human internal organ, which is sensed by the electronic skin quickly, accurately and in real-time when the piezoresistive electronic skin of the present invention is applied on the endoscopic medical system.

When implementing the embodiments of the invention, by the combination of nanostructure and new type nanomaterial, a sentient electronic skin device with high sensitivity, low energy consumption and high portability (wearable, attachable) may be formed, and new applications thereof, in various fields, may be researched and developed on the basis of physical characteristics of the piezoresistive electronic skin and the capacitive electronic skin. Thereinto, in the respect of sensing information from outside, the piezoresistive electronic skin has high-sensitivity sensing of small applied force from the outside, and the capacitive electronic skin may be applied on attachable electronic device and system to realize the acquisition of speech information, human physiology signals and the like. Therefore, the piezoresistive electronic skin and the ultrathin capacitive electronic device may be applied for achieving the real-time detection of human physiology signals (such as pulse, heart rate, breathing, blood pressure, and the like), and thereby achieving assessment of human health and previous diagnosis of diseases.

It should be explained that, in this document, relational terms such as the first, the second and the like are merely intended to distinguish an entity or an operation from another entity or operation, but not necessarily demand or mean that these entities or operations have any actual relationships or sequences therebetween. Furthermore, terms "comprise", "include" or any other variants are intended to cover non-exclusive inclusions, thereby resulting the processes, methods, articles or devices which comprise a series of elements not only comprise those elements, but also comprise other elements not clearly set out or comprise inherent elements of the processes, methods, articles or devices. The element, limited by a description "comprise a" but without further limitations, shall not exclude other identical elements existed in the processes, methods, articles or devices which comprise the elements. All the above are merely the preferred embodiments of the present invention, but are not to limit the invention in any form. Although the present invention has been described as above with reference to preferred embodiments, the intention is not to limit the present invention. Those skilled in the art may change or modify the above disclosed technical contents to obtain equivalent embodiments without departing from the scope of the present invention. The present invention is intended to cover all changes, various modifications and equivalent arrangements included within the principle and scope of the present invention according to the technical essence of the present invention.

What is claimed is:

1. A piezoresistive electronic skin, characterized by comprising:

a plurality of overlapped flexible substrates;

two conductive layers respectively arranged on two microstructure-patterned contact surfaces of adjacent flexible substrates and being contacted with each other, wherein contact areas of said conductive layers have non-planar microstructure; and conductive electrodes electrically connected with said two conductive layers;

wherein said conductive layer comprises a carbon nanotube film which comprises networks formed by cross-linked carbon nanotubes;

wherein said plurality of overlapped flexible substrates are made of one or a combination of more of the following materials: polydimethylsiloxane (PDMS) film, polyvinylidene fluoride (PVDF), polyvinyl fluoride (PVF), polyvinyl chloride (PVC), polyethylene (PE), polypropylene (PP), polystyrene (PS), polymethyl methacrylate (PMMA), nylon (Nylon), polycarbonate (PC), polyurethane (PU), polytetrafluoroethylene (PTFE), polyethylene terephthalate (PET, PETE), and high-polymer rubber materials.

2. The piezoresistive electronic skin according to claim 1, characterized in that at least one surface of said polydimethylsiloxane film is provided with patterns, the sizes of said patterns are between 0.1 and 500 μm, and the unit amount of said patterns in a square centimeter is between 1 and $10^{12}$.

3. The piezoresistive electronic skin according to claim 2, characterized in that said patterns are molded by coating said polydimethylsiloxane onto a template and solidifying it, said template is anyone of a silicon substrate provided with microstructure, a glass substrate provided with microstructure, a metallic substrate provided with microstructure, a plastic substrate, fabric or silk article provided with microstructure, and a bio-organ provided with microstructure.

4. The piezoresistive electronic skin according to claim 1, characterized in that the light transmittance of said carbon nanotube film is between 50% and 97%, and the sheet resistance is between $10^2$ Ω/sq and $10^7$ Ω/sq.

5. The piezoresistive electronic skin according to claim 4, characterized in that the thickness of said carbon nanotube film is between 10 nm and 500 nm, said carbon nanotube film is made of one type or a combination of more types of single-walled carbon nanotubes, double-walled carbon nanotubes and multi-walled carbon nanotubes, wherein said single-walled carbon nanotubes are metallic single-walled carbon nanotubes, semiconductor-type carbon nanotubes or hybrid single-walled carbon nanotubes containing both metallic single-walled carbon nanotubes and semiconductor-type carbon nanotubes.

6. The piezoresistive electronic skin according to claim 1, characterized in that said conductive layer is made of one or a combination of more of any conductive metal among copper, silver and gold, and semiconductor materials.

7. The piezoresistive electronic skin according to claim 1, characterized in that said conductive layer is attached with organic polymer material on the surfaces, said organic polymer material is one or a combination of more of materials as follows: polyvinylidene fluoride (PVDF), polyvinyl fluoride (PVF), polyvinyl chloride (PVC), polyethylene (PE), polypropylene (PP), polystyrene (PS), polymethyl methacrylate (PMMA), nylon (Nylon), polycarbonate (PC), polyurethane (PU), polytetrafluoroethylene (PTFE), polyethylene terephthalate (PET, PETE), polydimethylsiloxane (PDMS), and high-polymer rubber materials.

8. The piezoresistive electronic skin according to claim 1, characterized in that said conductive electrodes are made of one or a combination of more materials of gold, platinum, nickel, silver, indium, copper, carbon nanotube and graphene.

9. A preparation method of a piezoresistive electronic skin, characterized by comprising steps as follows:

S1. preparing two microstructure-patterned flexible substrates;

S2. preparing a solution for a conductive layer, respectively coating it to the microstructure-patterned surfaces of the two flexible substrates to form conductive layers, assembling the conductive layers by making the microstructure-patterned surfaces face to face to form a film device with the conductive layers being contacted with each other;

S3. forming upper, lower conductive electrodes respectively on the two conductive layers by conductive material, and leading wires from the conductive electrodes, thereby obtaining a piezoresistive electronic skin;

wherein the solution for the conductive layer is a solution of carbon nanotubes, and the conductive layer is made of carbon nanotube film.

10. The preparation method of the piezoresistive electronic skin according to claim 9, characterized in that at least one layer of said flexible substrates is made of polydimethylsiloxane film, and said flexible substrates in said step S1 are prepared by steps as follows:

S11. degassing polydimethylsiloxane in vacuum for 1-30 minutes and coating it onto a template provided with patterns, wherein the polydimethylsiloxane has a thickness of 0.1 mm to 3 mm, and then heating it for more than 0.5 hour at a temperature of 50° C. to 100° C. to solidify and mold it;

S12. removing the solidified and molded polydimethylsiloxane from the template by ultrasound in organic solvent for 5 to 30 minutes.

11. The preparation method of the piezoresistive electronic skin according to claim 10, characterized in that said template is chosen from a silicon substrate provided with microstructure, a glass substrate provided with microstructure, a metallic substrate provided with microstructure, a plastic substrate, fabric or silk article provided with microstructure, and a bio-organ provided with microstructure; said organic solvent may be methanol, ethyl alcohol and ethylene glycol.

* * * * *